(12) United States Patent
Lee

(10) Patent No.: US 9,114,239 B2
(45) Date of Patent: Aug. 25, 2015

(54) TATTOOING DEVICE

(75) Inventor: Jong-Dae Lee, Seocho-gu (KR)

(73) Assignee: Bomtech Electronics Co., Ltd., Seoul (KR)

( * ) Notice: Subject to any disclaimer, the term of this patent is extended or adjusted under 35 U.S.C. 154(b) by 870 days.

(21) Appl. No.: 13/386,330

(22) PCT Filed: Aug. 5, 2009

(86) PCT No.: PCT/KR2009/004373
§ 371 (c)(1),
(2), (4) Date: Jan. 20, 2012

(87) PCT Pub. No.: WO2011/010764
PCT Pub. Date: Jan. 27, 2011

(65) Prior Publication Data
US 2012/0123462 A1   May 17, 2012

(30) Foreign Application Priority Data

Jul. 22, 2009  (KR) .................... 10-2009-0068801

(51) Int. Cl.
*B43K 5/00*       (2006.01)
*A61M 37/00*   (2006.01)
*A61M 5/46*     (2006.01)

(52) U.S. Cl.
CPC ............. *A61M 37/0076* (2013.01); *A61M 5/46* (2013.01)

(58) Field of Classification Search
CPC ............. A61M 37/00; A61M 37/0076; A61B 2017/00473; A61B 2019/481; B65D 77/20
USPC .......... 81/9.22, 427.5, 177.1, 177.2; 606/185, 606/186
See application file for complete search history.

(56) References Cited

U.S. PATENT DOCUMENTS

| | | | |
|---|---|---|---|
| 4,719,825 A | | 1/1988 | LaHaye et al. |
| 5,776,158 A | * | 7/1998 | Chou .............................. 606/186 |
| 6,033,421 A | * | 3/2000 | Theiss et al. .................. 606/186 |
| 2003/0195542 A1 | * | 10/2003 | Lee ................. 606/186 |
| 2007/0060937 A1 | * | 3/2007 | Liu ............................. 606/185 |
| 2011/0048174 A1 | * | 3/2011 | Lin ................................. 81/9.22 |

FOREIGN PATENT DOCUMENTS

| | | |
|---|---|---|
| KR | 100444139 | 10/2003 |
| WO | 2008018781 A1 | 2/2008 |

* cited by examiner

*Primary Examiner* — Lee D Wilson
*Assistant Examiner* — Melanie Alexander
(74) *Attorney, Agent, or Firm* — Blank Rome LLP

(57) ABSTRACT

A tattooing apparatus includes a tattoo needle; and upward and downward moving means to transmit a rotating force of a driving motor to the tattoo needle. The upward and downward moving means consists of a cam structure to convert a rotary movement by the rotating force of a driving motor into a linear movement, and includes a bearing member for rolling contact to reduce vibrations and noises.

28 Claims, 17 Drawing Sheets

TATTOOING DEVICE

BACKGROUND OF THE INVENTION

1. Field of the Invention

The present invention relates to a tattooing apparatus, and more particularly, to a tattooing apparatus, which repeatedly inserts and takes out a tattoo needle, which is driven to repeatedly travel back and forth by a driving of motor, into and from a skin thus to penetrate a pigment for tattoo into the skin.

2. Description of the Related Art

In general, a tattooing apparatus is an apparatus, which represents a pattern or picture, such as signs, letters, and figures, on a skin of human by using a pigment for tattoo and a tattoo needle.

For convenience of tattoo procedures, a conventional tattooing apparatus is configured, so that the tattoo needle automatically travels back and forth and the pigment for tattoo rides the tattoo needle down while it travels back and forth. Here, since the tattoo needle moves while sticking at a given depth on the skin, a tattoo of given shape is represented on the skin as a practitioner intended.

A construction of such a conventional tattooing apparatus is as follows. Referring to FIGS. 1 and 2, the conventional tattooing apparatus 1 includes upper and lower casings 1a and 1b forming the exterior, a driving motor 3 installed in the upper casing 1a, a driving axis 3a of the driving motor 3 on which a cam surface 5a with a tilt angle is formed, a rotation bar 5 installed in the lower casing 1b by a hinge H1 to be rotatable left and right within a certain range by the cam surface 5a according to the rotation of the driving axis 51, a straight moving bar 7 having a coupling end 7a projected from and formed at one end thereof and coupled with one end of the rotation bar 5 by a hinge H2 to reciprocate in a straight line according to the left and right rotation of the rotation bar 5, and a tattoo needle 9 coupled to the other end of the straight moving bar 7.

According to the conventional tattooing apparatus 1 constructed as described above, when the driving axis 3a of the driving motor 3 rotates, the rotation bar 5, which repeatedly comes in contact with high and low surface portions of the cam surface 5a, is rotated left and right within the certain range, and thus the straight moving bar 7 reciprocates in the straight line to go in and out the tattoo needle 9 through a discharging hole on an lower end of the lower casing 1b.

However, since the conventional tattooing apparatus 1 as described above includes the separate rotation bar 5 for reciprocating the straight moving bar 7 in the straight line, the rotation of the rotation bar 5 synchronizes with the linear movement of the straight moving bar 7, thereby causing the tattooing apparatus to generate severe vibrations, which in turn make the practitioner difficult to exquisitely represent the tattoo.

Moreover, there was a problem in that the vibrations exert a load to the driving motor 3 to lower a driving output of the driving motor 2 and cause noises.

Also, there was a problem in that since the conventional tattooing apparatus 1 cannot adjust an exposed length of the tattoo needle 9, the practitioner has to possess each model of tattooing apparatus that a length where the tattoo needle 9 is exposed is different to perform the tattoo procedures.

SUMMARY OF THE INVENTION

Exemplary embodiment of the present invention addresses at least the above problems and/or disadvantages and provide at least the advantages described below. Accordingly, an aspect of the present invention is to provide a tattooing apparatus, which includes a cam link for offsetting a rotational inertia generated between a cam member and a connecting rod and which can reduce vibrations and noises by minimizing a friction force generated between the cam member and the cam link.

Another aspect of the present invention is to provide a tattooing apparatus, which can adjust an exposed length of a tattoo needle.

Further another aspect of the present invention is to provide a tattooing apparatus, which can block vibrations generated by parts operated for driving a tattoo needle to reciprocate in a straight line therein from being transmitted to a casing.

Also another aspect of the present invention is to provide a tattooing apparatus, which can maintain a sturdy combination between a needle slider and a connecting rod when they are assembled and which can quickly separate the needle slider and the cam link from each other by a simple operation when they are disassembled.

According to one aspect of an exemplary embodiment of the present invention, there is provided a tattooing apparatus, including a tattoo needle; and upward and downward moving means to transmit a rotating force of a driving motor to the tattoo needle, wherein the upward and downward moving means consists of a cam structure to convert a rotary movement by a rotating force of the driving motor into a linear movement, and comprises a bearing member for rolling contact to reduce vibrations and noises.

The upward and downward moving means preferably includes a cam member having a cam plate inclined to one side, the cam plate being rotatable by the driving motor; a connecting rod to transmit a power to the tattoo needle; and a cam link to travel back and forth in connection with the rotation of the cam member thus to transmit the power to the connecting rod, and the bearing member is preferably disposed at a side of the cam link to come in rolling contact with upper and lower ends of the one side of the cam plate.

The cam link may include a link column; an upper link bar projected at one side of the link column and hinged with one end of the connecting rod; and a pair of supporting protrusions projected at the one side of the link column and disposed in a spaced-apart relation with each other to allow the one side of the cam plate to be inserted therein. In this case, the bearing member is preferably made up of a pair of bearing members rotatably coupled to the pair of supporting protrusions, respectively, to come in rolling contact with upper and lower ends of the cam plate.

Further, the upward and downward moving means may include a cam member disposed to incline to one side; and a cam link disposed to pass through the cam member and having a rear end slidably inserted coaxial with a driving axis of the driving motor to rotate with the driving axis in connection with a rotation of the driving axis thus to transmit a power to a connecting rod, which in turn transmits the power to the tattoo needle.

In this case, the bearing member is preferably disposed at one side of the cam link to come in rolling contact with the cam member and disposed at a rear end of the connecting rod to come in rolling contact with a front end of the cam link.

Moreover, the upward and downward moving means may include a cam member having a cam plate driven to be rotated by the driving motor and disposed to incline to one side; and a cam link to transmit a power to a connecting rod, which in turn transmits the power to the tattoo needle, while reciprocally pivoting left and right in connection with a rotation of the cam member.

In this case, the bearing member is preferably disposed at a portion where the cam link and the cam member are in contact with each other.

The connecting rod may have a lower end hinged to a side of the cam link or configured to come in rolling contact with and by the bearing member.

The cam link is preferably in rolling contact with one of both sides of a cam plate through the bearing member.

The bearing member may be made up of a pair of roller bearings or a pair of ball bearings.

The tattooing apparatus may further include a first casing having the tattoo needle slidably accommodated therein; a second casing having the driving motor; and needle adjusting means to connect the first and the second casings and to adjust a degree where the tattoo needle is projected from the first casing by changing a coupling length between the first and the second casings to allow the first casing to approach the second casing or move away from the second casing.

The needle adjusting means may be made up of a rotation nut to rotate clockwise and counterclockwise.

The tattooing apparatus may further include an intermediate casing disposed in the first and the second casing to support the connecting rod, and providing a rotation groove in which the rotation nut is rotatably seated.

The needle adjusting means may further include an inner nut screwed coaxial with the rotation nut on an outer surface of the intermediate casing. The inner nut may have a stopper for maintaining rotation and constant position of the rotation nut, projected outward at a lower end thereof, and a threaded adjusting portion of a rear end of the first casing may be screwed with the rotation nut in a space between the inner nut and the rotation nut. The tattooing apparatus may further include a needle cartridge having a needle slider to support the tattoo needle, and the connecting rod may have a joint hooked and coupled with the needle slider to be capable of being separated therefrom and assembled therewith.

The joint may include an elongated rectangular joint hole in which a hanging hook projected from both sides of a lower end of the needle slider coupled is accommodated; and a hook hole formed to penetrate a side of the joint thus to allow the hanging hook to be fitted therein when the hanging hook rotates at an angle of 90 degrees along with the needle slider.

The connecting rod may be formed of a hollowed tube, and a linear reciprocating movement of the connecting rod may be guided by an anti-vibration tube wrapping the connecting rod. In this case, the anti-vibration tube may have an anti-vibration packing fitted between an inner side of the tattooing apparatus and an outer side of the anti-vibration tube to prevent vibrations and slips thereof.

According to another aspect of an exemplary embodiment of the present invention, there is provided a tattooing apparatus, including a tattoo needle; and upward and downward moving means to transmit a rotating force of a driving motor to the tattoo needle, wherein the upward and downward moving means includes a cam member having a cam plate driven to be rotated by the driving motor and disposed to incline to one side; and a cam link to transmit a power to a connecting rod, which in turn transmits the power to the tattoo needle, by reciprocally pivoting back and forth in connection with a rotation of the cam member.

In this case, the tattooing apparatus may further include a first casing having the tattoo needle slidably accommodated therein; a second casing having the driving motor; and needle adjusting means to connect the first and the second casings and to adjust a degree where the tattoo needle is projected from the first casing by changing a coupling length between the first and the second casings to allow the first casing to approach the second casing or move away from the second casing. At this time, the needle adjusting means is preferably made up of a rotation nut to rotate clockwise and counterclockwise.

The tattooing apparatus may further include an intermediate casing disposed in the first and the second casing to support the connecting rod, and providing a rotation groove in which the rotation nut is rotatably seated.

The needle adjusting means may further include an inner nut screwed coaxial with the rotation nut on an outer surface of the intermediate casing.

The inner nut may have a stopper for maintaining rotation and constant positions of the rotation nut, projected outward at a lower end thereof, and a threaded adjusting portion of a rear end of the first casing may be screwed with the rotation nut in a space between the inner nut and the rotation nut.

The tattooing apparatus may further include a needle cartridge having a needle slider to support the tattoo needle, and the connecting rod preferably has a joint hooked and coupled with the needle slider to be capable of being separated therefrom and assembled therewith.

The joint may include an elongated rectangular joint hole in which a hanging hook projected from both sides of a lower end of the needle slider coupled is accommodated; and a hook hole formed to penetrate a side of the joint thus to allow the hanging hook to be fitted therein when the hanging hook rotates at an angle of 90 degrees along with the needle slider.

The connecting rod may be formed of a hollowed tube, and a linear reciprocating movement of the connecting rod may be guided by an anti-vibration tube wrapping the connecting rod. The anti-vibration tube may have an anti-vibration packing fitted between an inner side of the tattooing apparatus and an outer side of the anti-vibration tube to prevent vibrations and slips thereof.

According to the aspects of the exemplary embodiment of the present invention, there is an advantage in that a bearing is disposed between a connecting rod and a cam member, which are operated in connection with each other to enable a tattoo needle to reciprocate, to induce the connecting rod and the cam member to come in rolling contact with each other, thereby minimizing vibrations and noises generated in driving and loads transmitted to the driving motor due to friction force between the cam link and the cam member to prevent the driving motor from being lowered in driving output and to decrease power consumption thus to maximize usability.

Further, there is an advantage in that as a needle adjusting means of the tattoo needle disposed between the first and the second casings is rotated, the exposed length of the tattooing apparatus can be easily adjusted.

Moreover, there is an advantage in that as the body of the connecting rod, which are operated in connection with each other to reciprocate the tattoo needle, is formed of a small tube, and at circumferences thereof, coaxially fitted with the anti-vibration tube, to prevent the vibrations from being transmitted to the casing and to enable the link to move straight, thereby causing no obstruction to the use of the tattooing apparatus due to the vibrations.

Also, there is an advantage in that the joint detachably coupling the needle slider and the connecting rod is coupled and separated by using the hook connection, thereby allowing the components to be easily separated and not requiring separate parts for assembling.

DETAILED DESCRIPTION OF THE PREFERRED EMBODIMENT

Hereinafter, a configuration of an tattooing apparatus according to exemplary embodiments of the present invention will now be described in greater detail with reference to the accompanying drawings.

Figure 1:
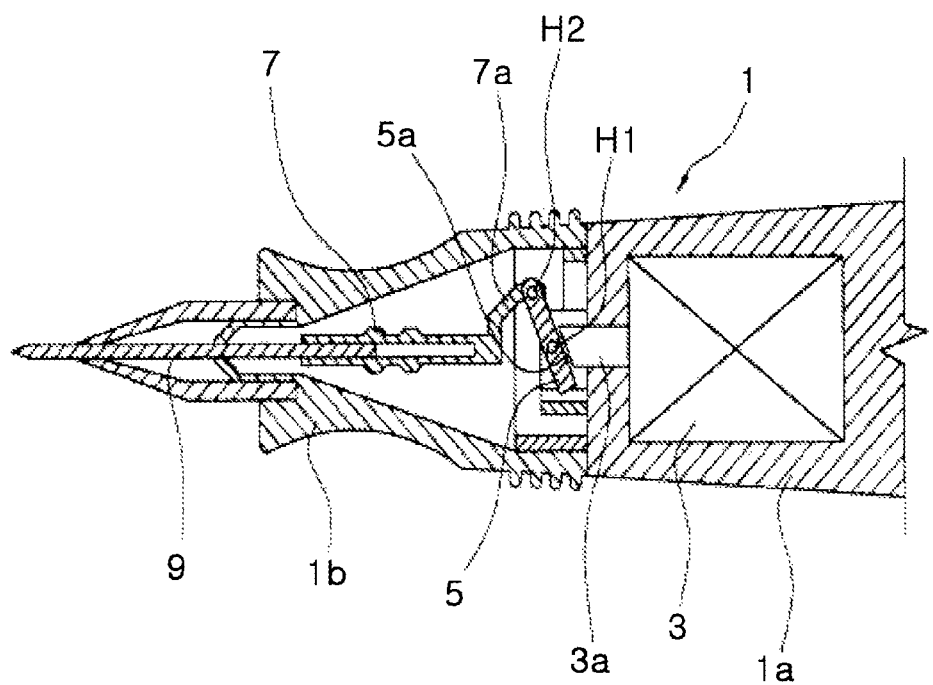
FIG. 1 is a cross-sectional view showing an example of a conventional tattooing apparatus.
Figure 2:
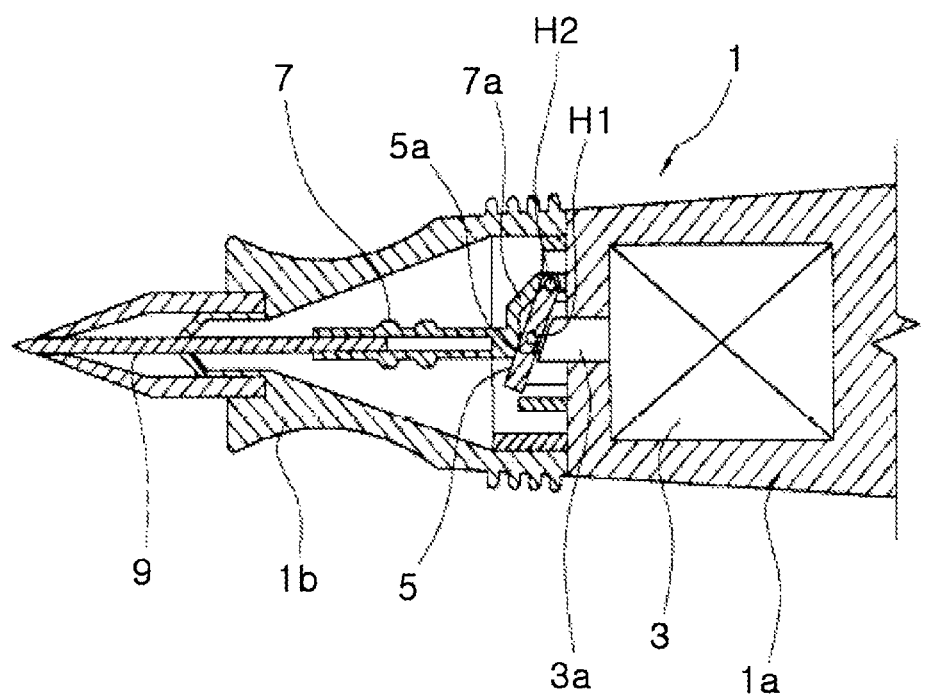
FIG. 2 is a cross-sectional view illustrating the tattooing apparatus shown in FIG. 1, in a state where it is used.
Figure 3:
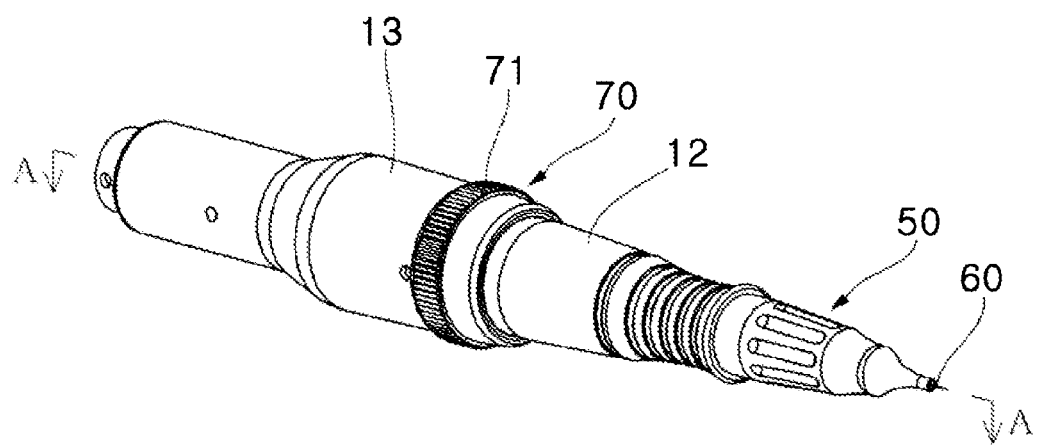
FIG. 3 is a perspective view showing a tattooing apparatus according to an exemplary embodiment of the present invention.
Figure 4:
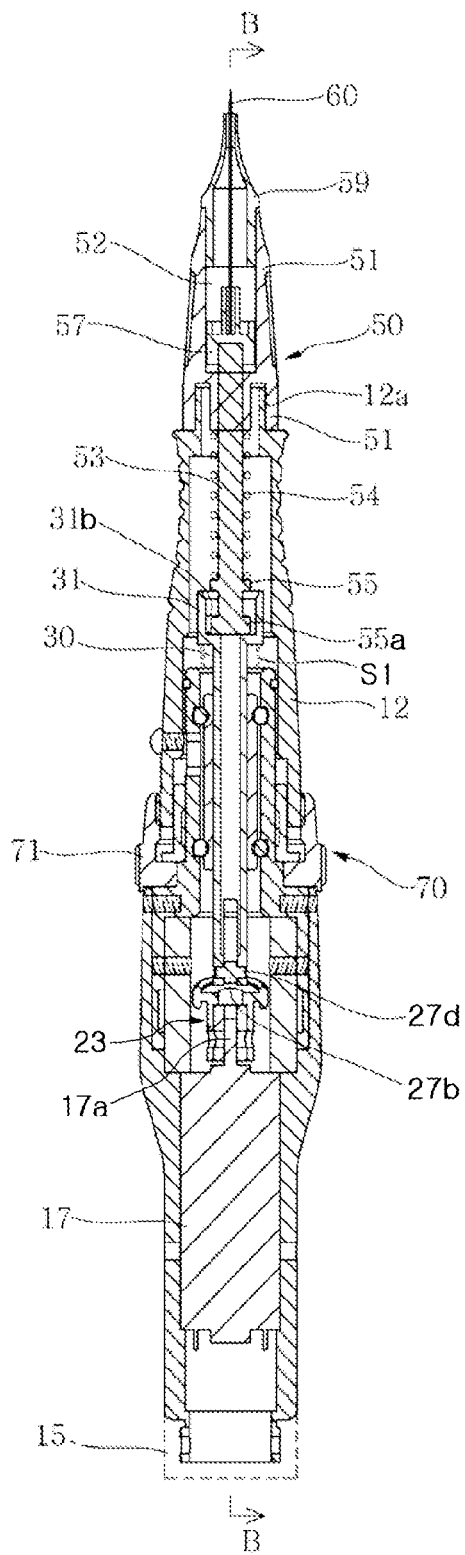
FIG. 4 is a cross-sectional view taken along line A-A shown in FIG. 3.
Figure 5:
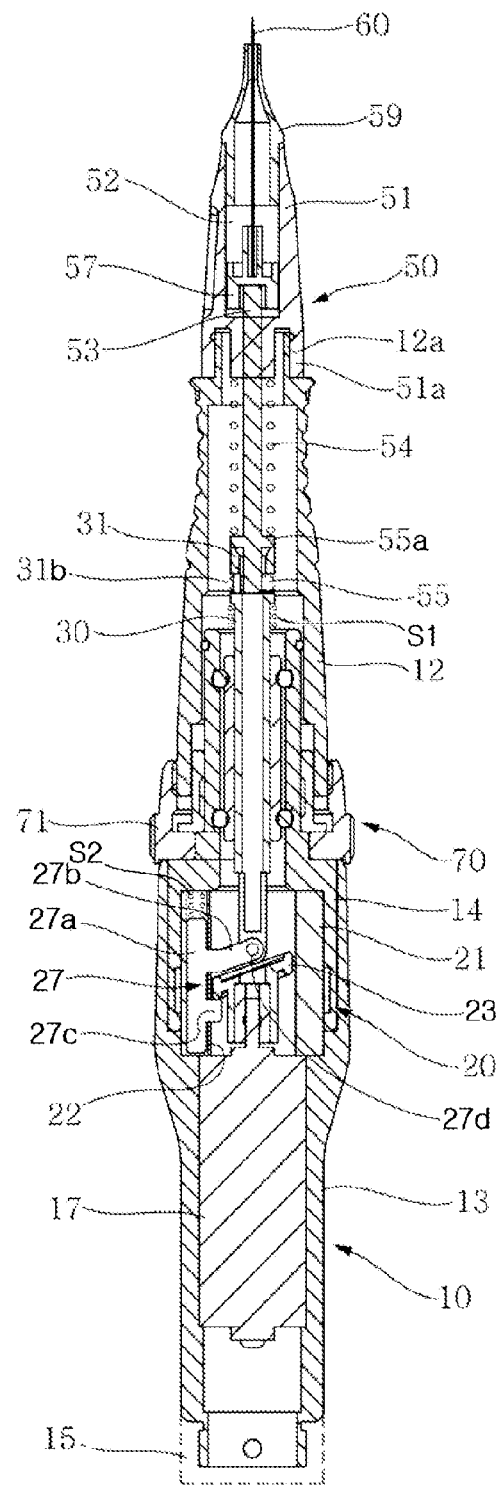
FIG. 5 is an exploded perspective view showing a joint of the tattooing apparatus according to the exemplary embodiment of the present invention in a state before it is assembled.
Figure 6:
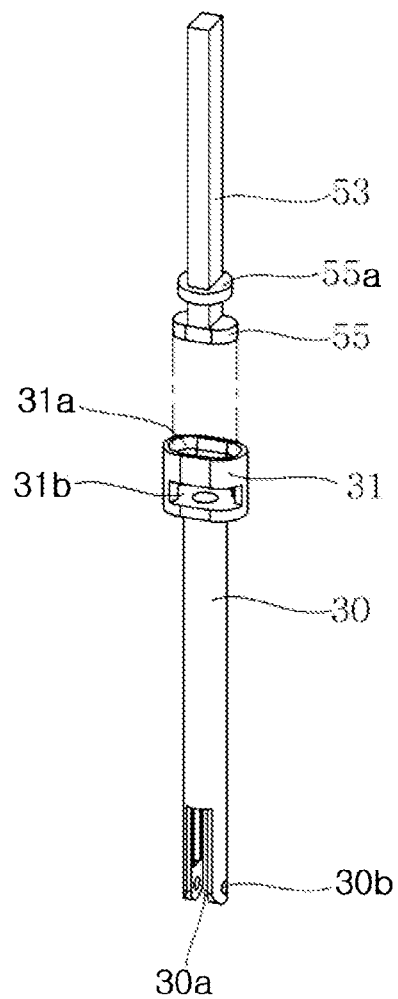
FIG. 6 is a cross sectional view taken along line B-B shown in FIG. 4.
Figure 7:
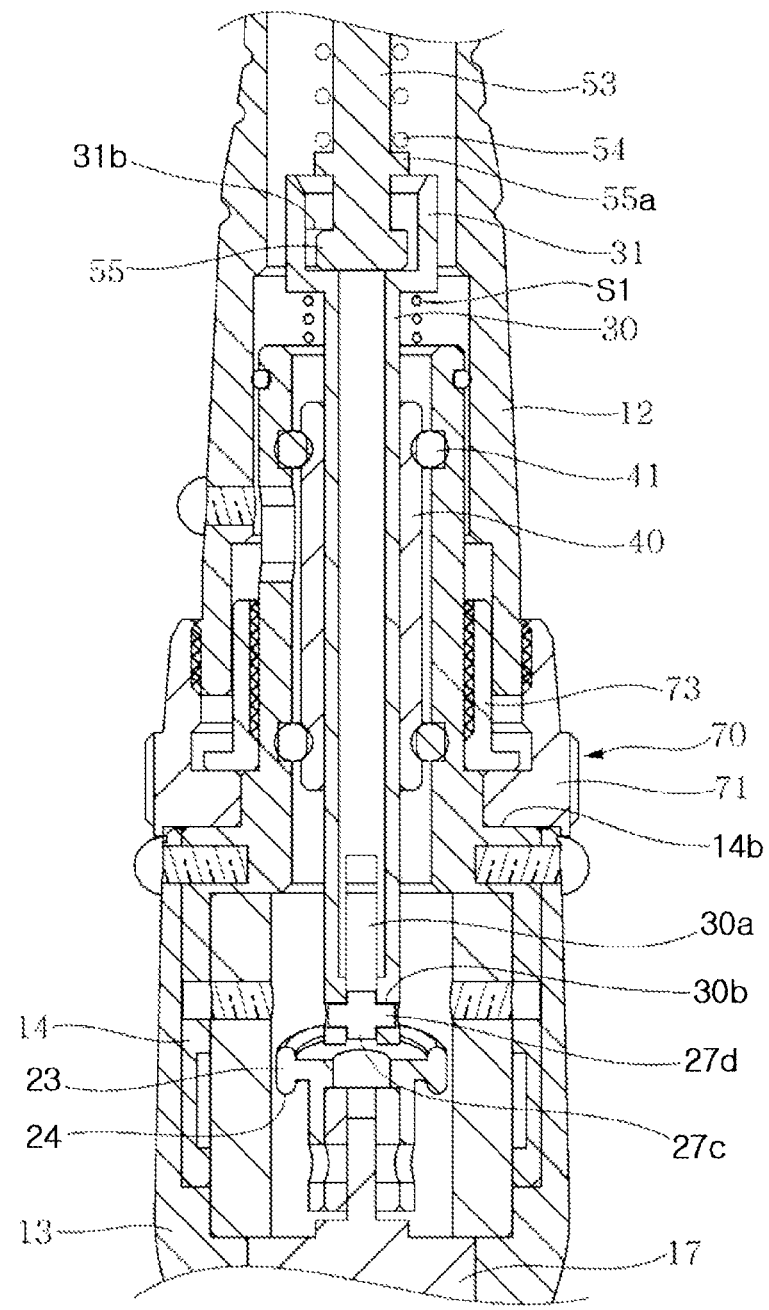
FIG. 7 is an enlarged view showing main parts of FIG. 4.
Figure 8:
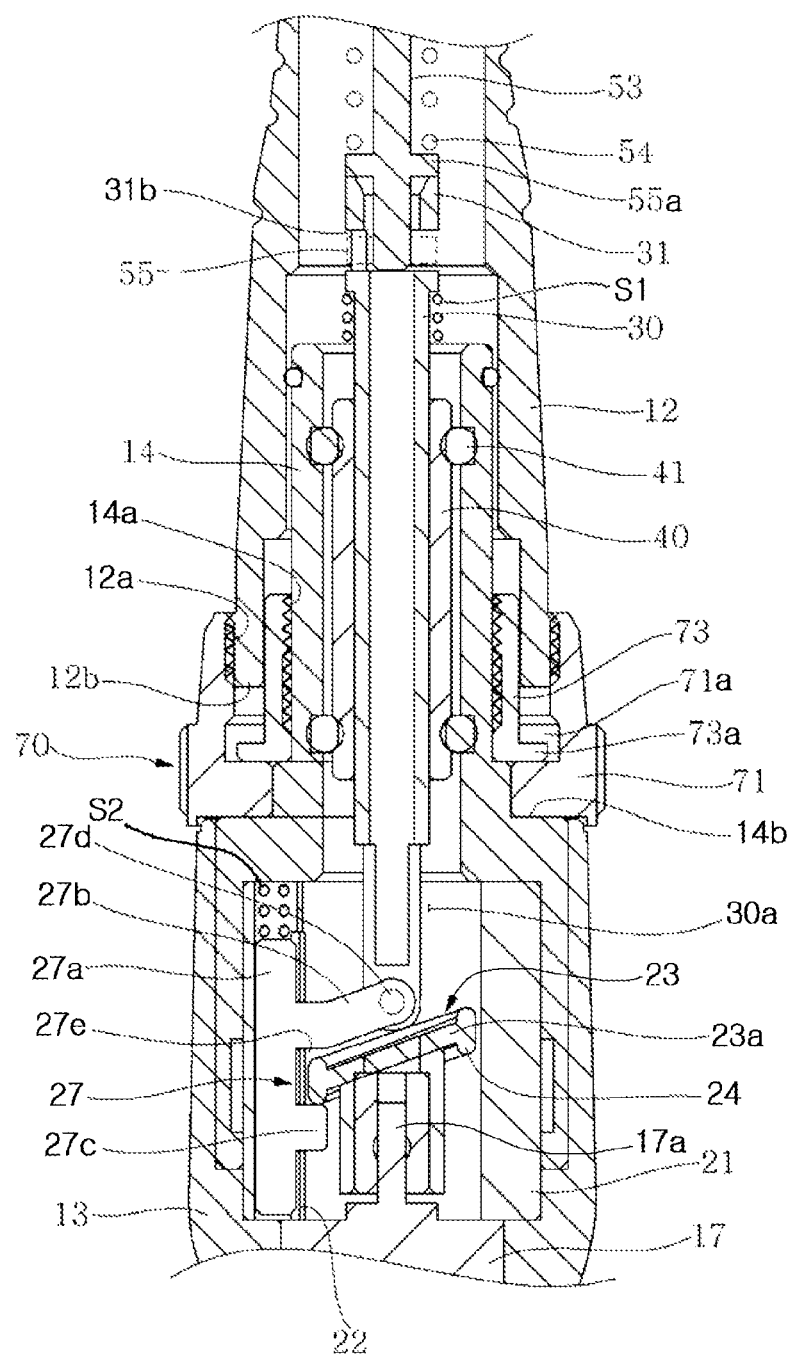
FIG. 8 is an enlarged view showing main parts of FIG. 5.
Figure 9:
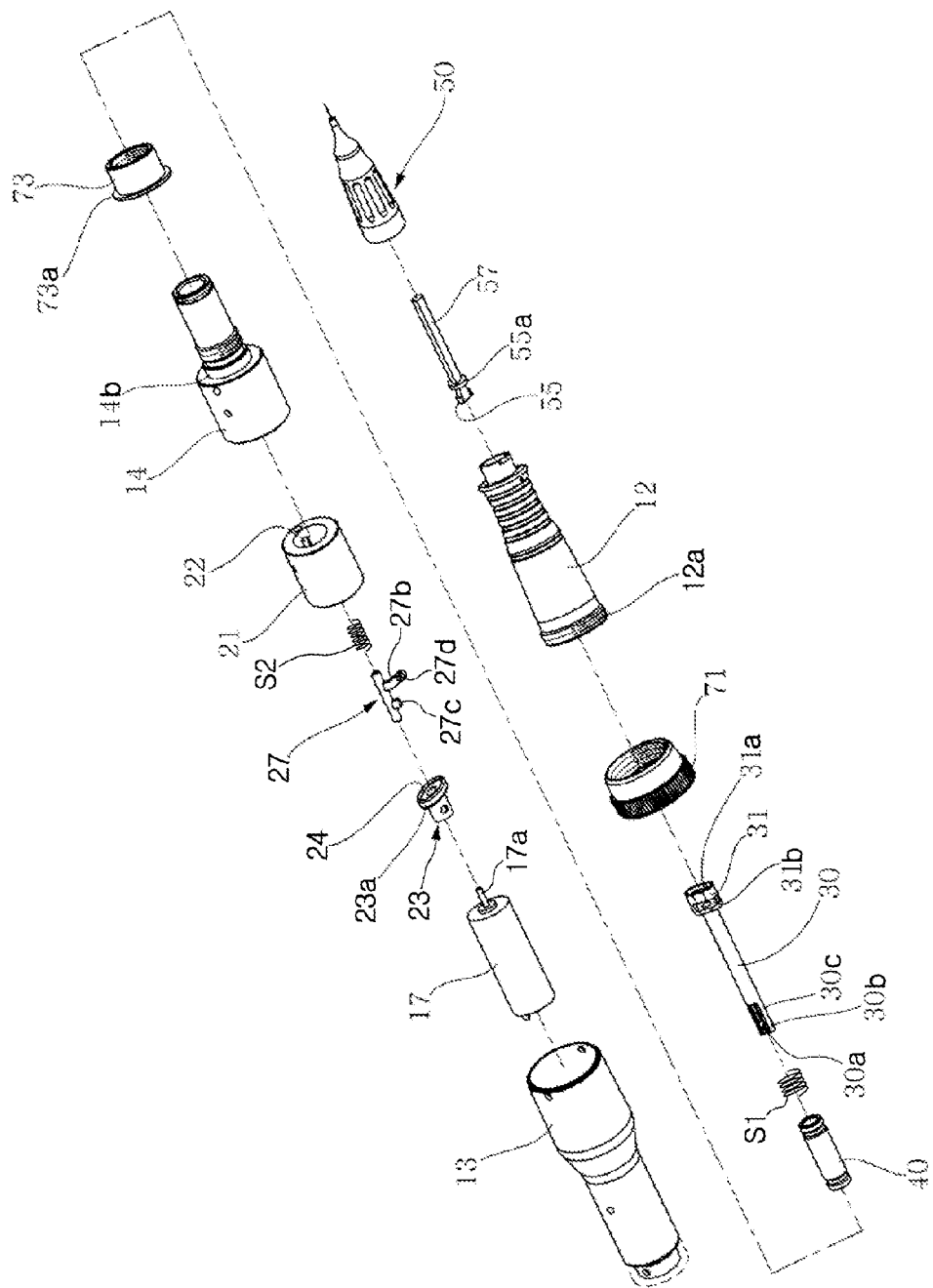
FIG. 9 is an exploded perspective view showing the tattooing apparatus according to the exemplary embodiment of the present invention.

In the accompanying drawings, FIG. 3 is a perspective view showing a tattooing apparatus according to an exemplary embodiment of the present invention, FIG. 4 is a cross-sectional view taken along line A-A shown in FIG. 3, FIG. 5 is a cross-sectional view taken along line B-B shown in FIG. 4, FIG. 6 is an exploded perspective view showing a joint of the tattooing apparatus according to the exemplary embodiment of the present invention in a state before it is assembled, FIG. 7 is an enlarged view showing main parts of FIG. 4, FIG. 8 is an enlarged view showing main parts of FIG. 5, and FIG. 9 is an exploded perspective view showing according to the exemplary embodiment of the present invention.

As shown in FIG. 3, the tattooing apparatus according to the exemplary embodiment of the present invention includes a first casing 12, a second casing 13, an intermediate casing 14, upward and downward moving means 20, a connecting rod 30, a needle cartridge 50, and needle adjusting means 70.

Referring to FIGS. 4 and 5, The first casing 12 is coupled to the needle cartridge 50, so that it accommodates the connecting rod 30, which drives to reciprocate a needle slider 53.

The second casing 13 is coupled with the first casing 12, and accommodates the upward and downward moving means 20 having a cam structure for reciprocation of the connecting rod 30, and a driving motor 17.

The intermediate casing 14 provides a rotation groove 14b disposed in a connection portion between the first and the second casings 12 and 13 and having one side to which a rotation nut 71 forming the needle adjusting means 70 is rotatably coupled. In this case, the intermediate casing 14 allows the connecting rod 30 to pass therethrough and at the same time, supports the connecting rod 30 to be slidable.

The upward and downward moving means 20 includes a fixing tube 21, a cam member 23, a curved dam 24, and a cam link 27.

The fixing tube 21 is fixedly disposed in the intermediate casing 14, and has an upward and downward guiding groove 22 formed at an inner circumferential surface thereof to guide the cam link 27 to move up and down.

To carry out a cam function, the cam member 23 at a front end thereof has a cam plate 23a inclined to one side and at a rear end thereof is coupled with a driving axis 17a of the driving motor 17 to rotate according to a driving of the driving motor 17.

The curved dam 24 is formed at and projected from a predetermined height above and below along an edge of the cam plate 23a, and upper and lower ends of the curved dam 24 is in point contact with upper and lower link bars 27b and 27c therebetween.

The cam link 27 includes the upper and the lower link bars 27b and 27c, which slidably move along a surface of the curved dam 24, and a square-shaped link column 27a, which integrally combines the upper and the lower link bars 27b and 27c. In this case, the upper link bar 27b at one end thereof has hinge protrusions 27d projected from both sides thereof and fitted in and with a lower end of the connecting rod 30. Further, the link column 27a is preferably formed of a square column or a oval column, so that it can move up and down, but cannot rotate.

Since the curved dam 24 is disposed to be in point contact with the upper and the lower link bars 27b and 27c therebetween, the cam link 27 travels at a predetermined distance up and down as the upper and the lower link bars 27b and 27c move up and down along the surface of the curved dam 24 when the cam member 23 rotates.

The connecting rod 30 has a body formed of a hollowed tube, and has a structure with a joint 31, which is hooked and coupled with one end of the needle slider 53 to be capable of being assembled therewith and separated therefrom.

In this case, an anti-vibration tube 40 is disposed to wrap an outer side of the connecting rod 30, and thus guides an upward and downward linear movement of the connecting rod 30 between the connecting rod 30 and the intermediate casing 14. At this time, anti-vibration packings 41 are fitted to an outer surface of the anti-vibration tube 40 and an inner surface of the intermediate casing 14 therebetween to prevent vibrations and slips therebetween.

On the other hand, first and second coil springs S1 and S2 are disposed on an upper side of the connecting rod 30 and an upper end of the cam link 27, respectively. The first coil spring S1 absorbs impacts due to inertia when the link mechanism is moved in a backward direction, and the second coil spring S2 absorbs impacts due to inertia when the link mechanism is moved in a forward direction, thereby reducing vibrations and noises.

The joint 31 includes an elongated rectangular joint hole 31a in which a hanging hook 55 projected from both sides of a lower end of the needle slider 53 is accommodated, and a hook hole 31b formed to penetrate a side of the joint hole 31a thus to allow the hanging hook 55 to be fitted therein when it rotates at an angle of 90 degrees along with the needle slider 53 as it penetrates the side of the joint hole 31a along with the needle slider 53.

Further, the connecting rod 30 has a slit 30a formed at a lower end thereof to make side walls 30c face parallel to each other, and hinge holes or grooves 39b in which the hinge protrusions 27d are fitted are formed on the facing side walls 30c.

The needle cartridge 50 is provided with the tattoo needle 60, and the needle slider 53 to drive the tattoo needle 60.

The needle adjusting means 70 connects the first casing 12 and the second casing 13, and as it rotates clockwise and counterclockwise, adjusts a degree where the tattoo needle 60 is projected from the first casing 12 by changing a coupling length between the first and the second casings 12 and 13 to allow the first casing 12 to approach the second casing 13 or move away from the second casing 13

The needle adjusting means 70 as described above further include an inner nut 73 screwed coaxial with the rotation nut 71 on an outer surface of the intermediate casing 14. The inner nut 73 has a stopper 73a for maintaining rotation and constant positions of the rotation nut 71, which is projected outward at a lower end thereof. In this case, a threaded adjusting portion 12a of a rear end 12b of the first casing 12 is screwed with the rotation nut 71 in a space 71a between the inner nut 73 and the rotation nut 71.

In assembling of the tattoo apparatus configured as described above, the hanging hook 55, which is a lower end of the needle slider 53, is lowered toward the joint hole 31a, as shown in FIG. 6. After the hanging hook 55 is lowered, a cartridge body 51 is rotated at an angle of 90 degrees and thus the hanging hook 55 is hooked and coupled in the hook hole 31b to be fitted therein.

Here, the first casing 12 and the needle cartridge 50 coupled thereto, which guide to take out the tattoo needle 60 at a certain projected or taken-out length, are adjusted in length by the needle adjusting means 70. This acts to reduce and increase the tattoo needle 60 in length.

For instance, if the rotation nut 71 is rotated in an unscrewed direction, the threaded adjusting portion 12a acts to increase the first casing 12 in length, instead of moving the rotating rotation nut 71, while being unscrewed. Accordingly, this means that the exposed length of the tattoo needle 60 is reduced.

To the contrary, if the rotation nut 71 is rotated in a screwed direction, the first casing 12 exerts an pulling action to the rotating rotation nut 71, and thus the exposed length of the tattoo needle 60 is relatively lengthened. This enables the tattoo needle 60 to be adjusted and used in variously exposed length according to portions and conditions of the skin where the practitioner tattoos. Accordingly, by variously adjusting the exposed length of the tattoo needle 60, the tattooing apparatus can combine various models by using one, thereby bringing economical benefit.

On the other hand, the tattooing apparatus of the exemplary embodiment of the present invention is configured, so that the curved dam 24 curved above and below is formed at the edge of the cam plate 23a to allow upper and lower portion thereof to be driven in point contact with the upper and the lower link bars 27b and 27c and thus to allow the cam link 27 to exert an upward and downward action, which applies a reciprocating movement to the needle slider 53 and the tattoo needle 60 through the connecting rod 30, thereby reducing the driving motor 17 in load to decrease power consumption and removing noises. Further, the cam link 27 is formed of a rectangular or oval shape, so that it is always moved up and down without being rotated, thereby providing stability and good assembling ability.

Moreover, as shown in FIG. 8, the hinge protrusions 27d are exposed at both sides of the upper end of the upper link bar 27b, and fitted in the hinge grooves 30b of the side walls 30c separated from to each other by the slit 30a, so that the side walls 30c and the hinge protrusions 27d are not separated from each other, but moved up and down in a body. In other words, the upper link bar 27b is fitted in the slit 30a of same size, and in assembling, the slit 30a is spread a little to allow the hinge protrusions 27d to be coupled in the hinge grooves 30b. In the end, the hinge protrusions 27d assembled remains as it is, and the upper link bar 27b maintains a state where it is in contact with an inner surface of the slit 30a not to be separated from the slit 30a in use, thereby continuing stable action.

On the other hand, the tattooing apparatus of the exemplary embodiment of the present invention is configured, so that the body of the connecting rod 30 is formed of a tube of small diameter and at circumferences thereof, fitted with the anti-vibration tube 40, and the anti-vibration tube 40 is coupled with the intermediate casing 14 through the anti-vibration packings 41 in a state where it prevents the inner surface of the intermediate casing 14 from generating slips and where it allows the inner surface of the intermediate casing 14 to absorb vibrations, thereby enabling the connecting rod 30 to move straight and at the same time, absorbing impact vibrations through the anti-vibration tube 40 and the anti-vibration packings 41 twice over to prevent the vibrations from being transmitted even to the first casing 12 and thus to maximize using sensitivity of the user and remove noises due to the vibrations.

In the tattooing apparatus of the exemplary embodiment of the present invention as described above, for the sake of convenient assembly and disassembly, a threaded inner nut-fixing portion 14a is formed on the intermediate casing 14 to coaxially assemble the inner nut 73 with the rotation nut 71.

Further, a stopper 73a is projected from the inner nut 73, so that it blocks the rotation nut 71 seated in the rotation groove 14b from moving to the first casing 12 and so that in disassembling, the rotation nut 71 is unscrewed to first separate the first casing 12 and then the inner nut 73 is unscrewed to separate the rotation nut 71 from the intermediate nut 14, thereby allowing the tattooing apparatus to be assembled and disassembled. Also, the rear end 12b of the first casing 12 is disposed in the space 71a between the inner but 73 and the rotation nut 71, and is screwed with the rotation nut 71 by the threaded adjusting portion 12a to be coupled at the inner and outer surface of the first casing 12, thereby maximizing coupling force therebetween.

Although the tattooing apparatus of the exemplary embodiment of the present invention has been explained based on penetrating a tattoo ink for tattoo into the skin through the tattoo needle, it can be also used for injecting an injectable solution or a drug into the skin.

On the other hand, although the cam link 27 as described above has been illustrated as being in direct point contact with the curved dam 24 of the cam member 23, the present invention is not limited thereto, and bearings are disposed on contact portions between the cam link 27 and the cam member 23 to minimize a friction force between the cam link 27 and the cam member 23.

Figure 10:
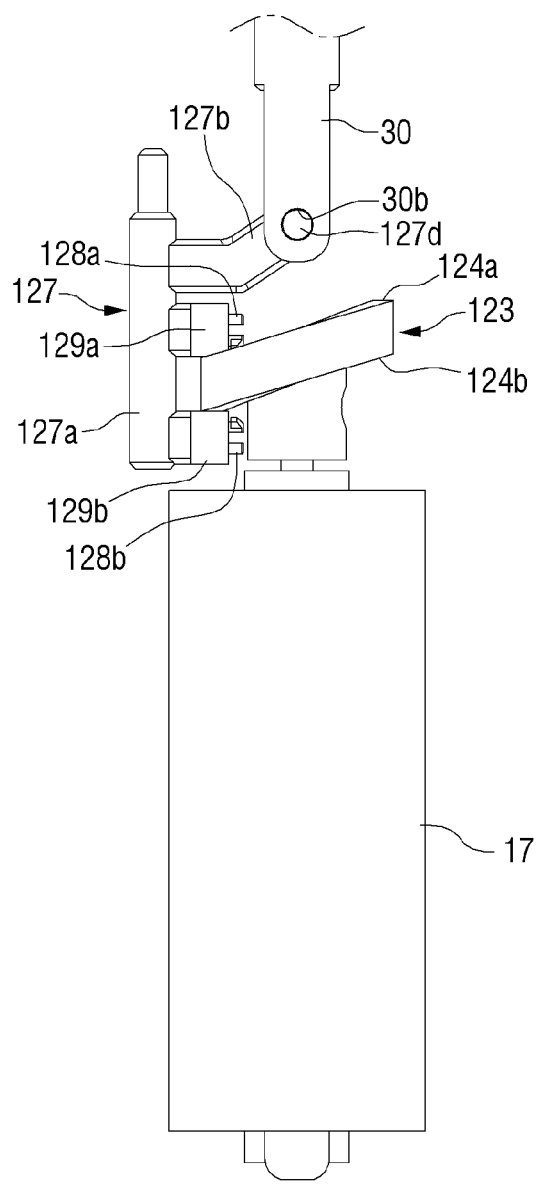
FIGS. 10 to 12 are a side elevation, a cross-sectional view, and an exploded perspective view showing an example of a cam link to which a cylindrical bearing is employed, respectively.
Figure 11:
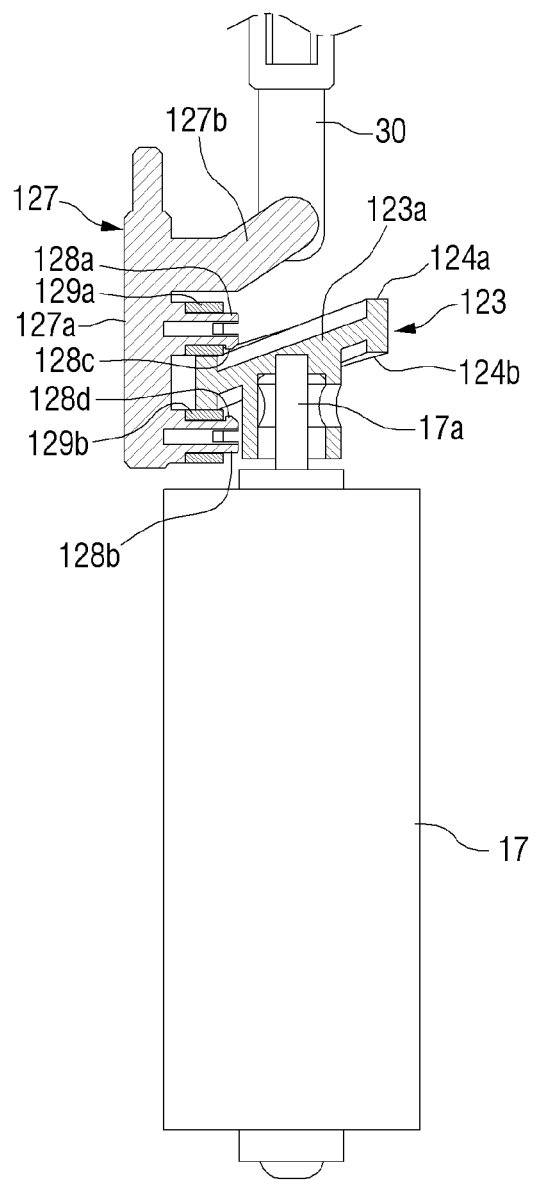
Figure 12:
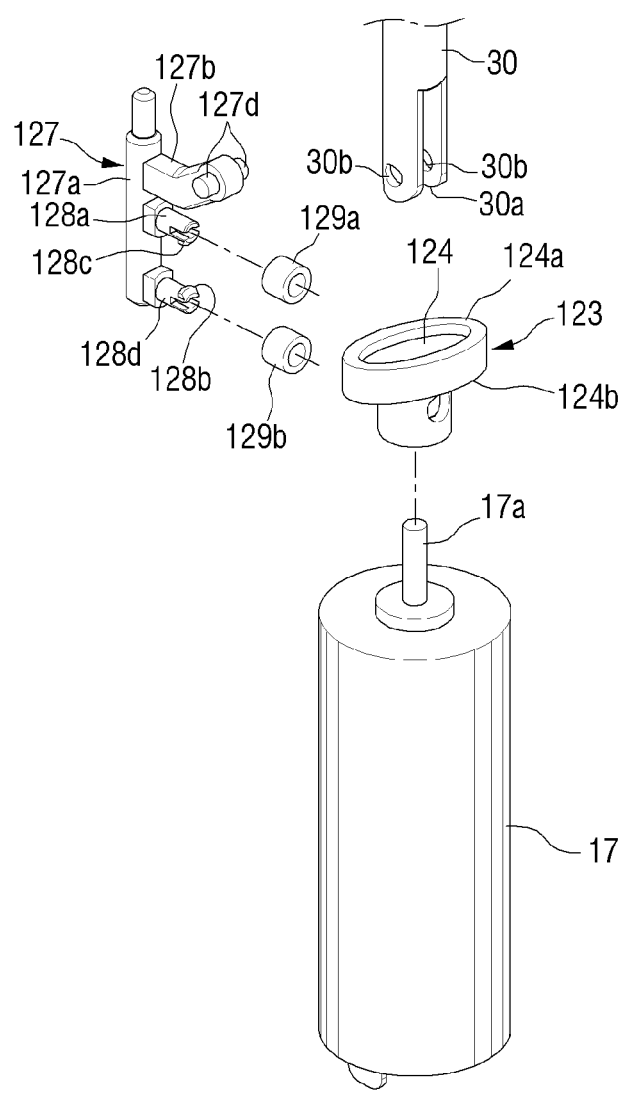

Hereinafter, an example wherein a roller bearing among various bearing structures is employed in the cam link will be explained in detail with reference to FIGS. 10 to 12. FIGS. 10 to 12 are a side elevation, a cross-sectional view, and an exploded perspective view showing an example wherein roller bearings are employed in the cam link of the present invention, respectively.

The cam link 127 at an upper part thereof is formed the upper link bar 127b, which is hinged with the connecting rod 30. On the other hand, a pair of supporting protrusions 128a and 128b is projected approximately perpendicular to a longitudinal direction of the cam link 127 while spacing down from the upper link bar 127b, and roller bearings 129a and 129b are snapped and coupled on the supporting protrusions 128*a* and 128*b*, respectively. At this time, hanging jaws 128*c* and 128*d* are formed on end tips of the pair of supporting protrusions 128*a* and 128*b* to prevent the roller bearings 129*a* and 129*b* from being released from the pair of supporting protrusions 128*a* and 128*b*, respectively.

The pair of roller bearing 129*a* and 129*b* is rotatably coupled on the supporting protrusions 128*a* and 128*b*, and a portion of the curved dam 124 of the cam member 123 is inserted between the pair of roller bearing 129*a* and 129*b*. In this case, if the cam member 123 is rotated according to the driving of the driving motor 17, the upper and the lower ends 124*a* and 124*b* of the curved dam 124 are slid in a state where they come in contact with the pair of roller bearing 129*a* and 129*b*, respectively. According to this, the friction force generated between the cam member 123 and the cam link 127 can be minimized, thereby greatly reducing the vibrations and the noises and at the same time, minimizing driving output of the driving motor 17.

Although the bearing structure as described above has been explained as employing the roller bearings, it can also employ ball bearings different therefrom.

Figure 13:
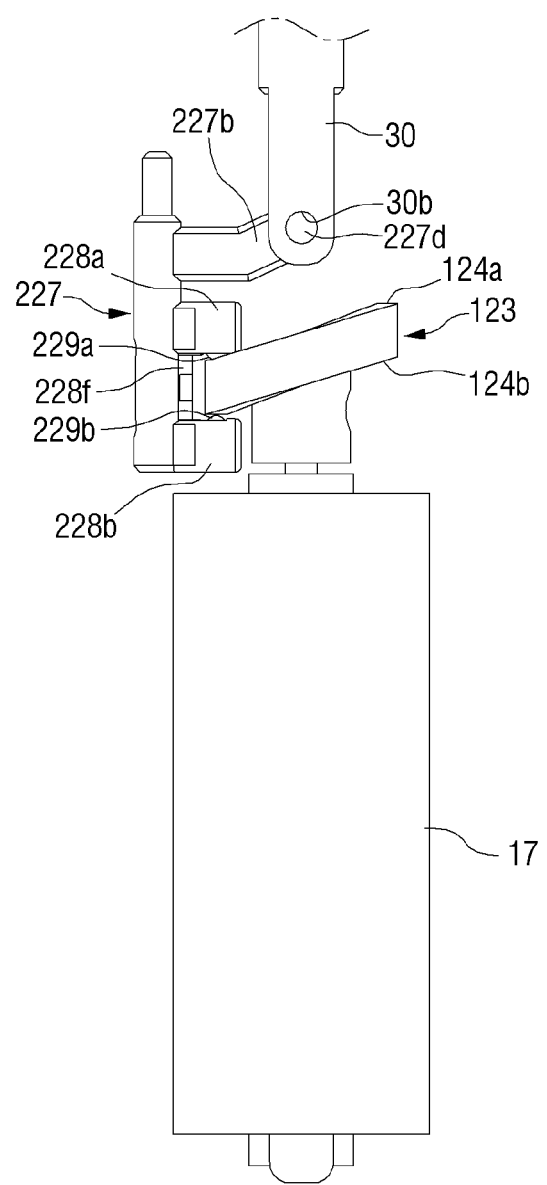
FIGS. 13 to 15 are a side elevation, a cross-sectional view, and an exploded perspective view showing an example of a cam link to which a ball bearing is employed, respectively.
Figure 14:
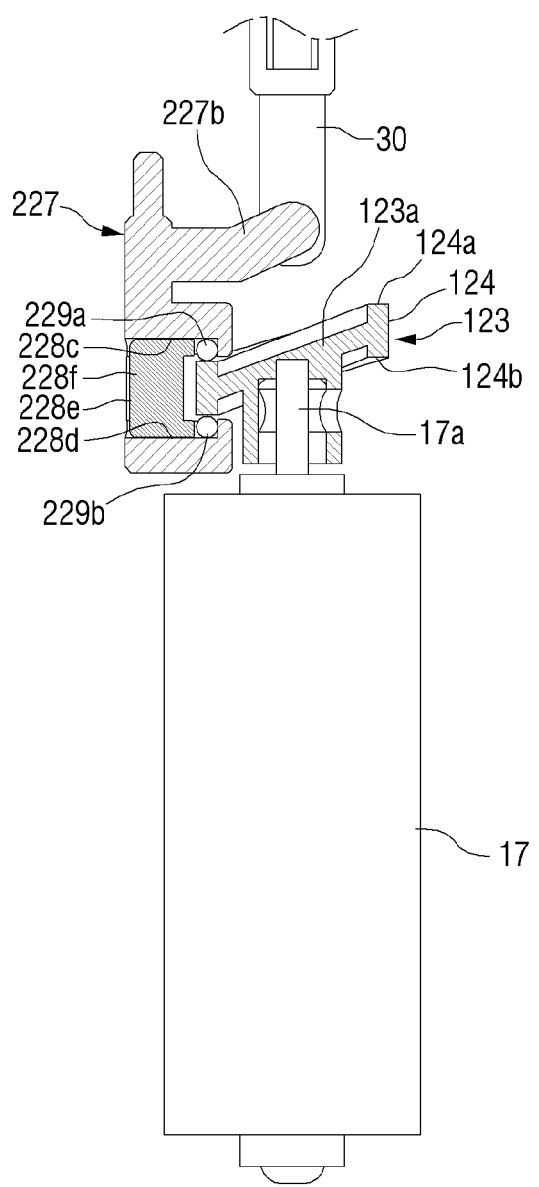
Figure 15:
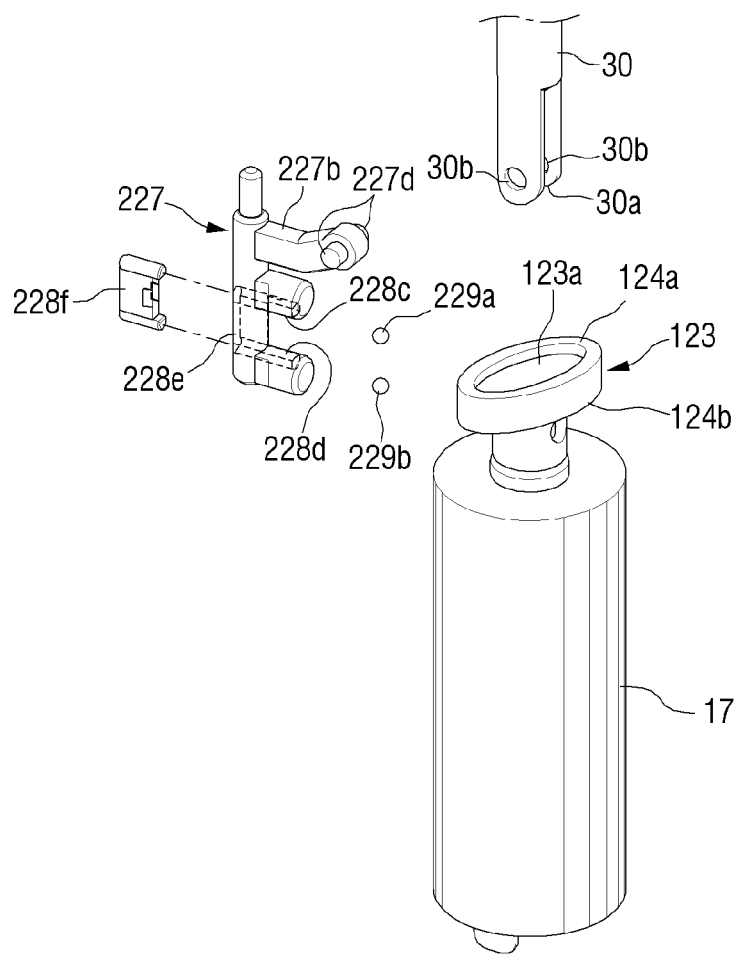

Hereinafter, an example where the ball bearings are employed in the cam link will be explained in detail with reference to FIGS. 13 to 15. FIGS. 13 to 15 are a side elevation, a cross-sectional view, and an exploded perspective view showing an example where the roller bearings are employed in the cam link of the present invention, respectively.

The cam link 227 at an upper part thereof is formed the upper link bar 227*b*, which is hinged with the connecting rod 30. On the other hand, a pair of supporting protrusions 228*a* and 228*b* is projected approximately perpendicular to a longitudinal direction of the cam link 227 while spacing down from the upper link bar 227*b*. Recessed grooves 228*c* and 228*d* are formed on inner sides of the pair of supporting protrusions 228*a* and 228*b* in a direction facing each other, and the ball bearings 229*a* and 229*b* are rotatably inserted in the recessed grooves 228a and 228*b*, respectively.

In this case, to prevent the pair of ball bearings 229*a* and 229*b* from being released to one side of the cam link 227, a stopper 228*f* rotatably supports the pair of ball bearings 229*a* and 229*b* in a state where it is inserted into an inserting hole 228*e*.

According to this, a portion of the curved dam 124 of the cam member 123 is inserted between the pair of roller bearing 229*a* and 229*b*. If the cam member 123 is rotated according to the driving of the driving motor 17, the upper and the lower ends 124*a* and 124*b* of the curved dam 124 are slid in a state where they come in contact with the pair of roller bearing 229*a* and 229*b*, respectively. As a result, like in case of employing the roller bearings 129*a* and 129*b*, the friction force generated between the cam member 123 and the cam link 227 can be minimized, thereby greatly reducing the vibrations and the noises and at the same time, minimizing driving output of the driving motor 17.

Figure 16:
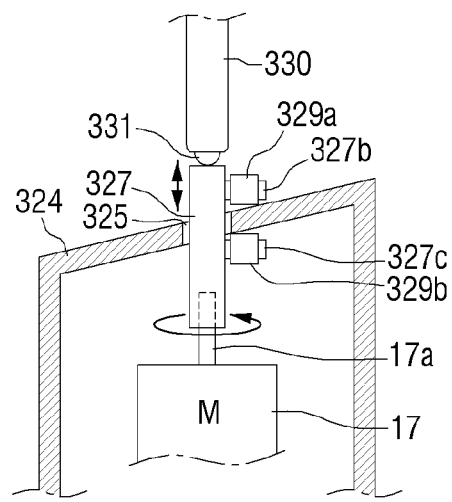
FIGS. 16 to 19 are views showing various examples of a cam structure capable of being applied to the present invention.
Figure 17:
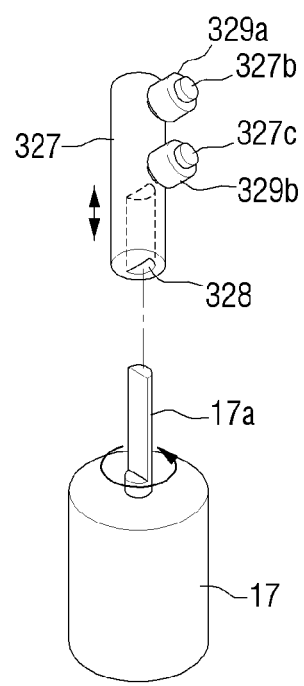

On the other hand, as shown in FIGS. 16 and 17, the cam structure of the present invention may be constructed in various ways, and in this case, the bearings can be also employed to components, which comes in sliding contact with the cam member, thereby minimizing the vibrations and the noises.

First, a cam structure shown in FIGS. 16 and 17 is configured, so that the driving axis 17*a* of the driving motor 17 is inserted an inserting groove 328 formed on a rear end of a cam link 328. In this case, the driving axis 17*a* and the inserting groove 328 are cut out at one sides thereof, so that when the driving axis 17*a* rotates, the cam link 327 rotates along with he driving axis 17*a* and at the same time, moves back and forth along an axial direction of the driving axis 17*a*.

Further, a connecting rod 330 is disposed on the same axial line as the cam link 327, and a pair of supporting protrusions 327*b* and 327*c* is formed at one side of the cam link 327 in the same direction. The pair of supporting protrusions 327*b* and 327*c* has roller bearings 329*a* and 329*b* rotatably installed thereon, respectively. In this case, besides the roller bearings 329*a* and 329*b*, ball bearings may be also applied. Moreover, as a ball bearing 331 installed on a rear end of the connecting rod 330 is disposed in contact with a front end of the cam link 327, the cam link 327 and the connecting rod 330 come in rolling contact with each other.

A cam member 324 is disposed to incline to one side, and at a middle thereof is formed a penetrated hole 325 through which the cam link 327 passes. Also, the cam member 324 is fixedly installed in the intermediate casing 14.

In the cam structure constructed as described above, when the driving motor 17 rotates, the cam link 327 is rotated along with the driving axis 17*a* by the cam member 324 and at the same time, the connecting rod 330 is also traveled back and forth along with the cam link 327. Friction forces generated between the cam link 327 and the cam member 324 and between the cam link 327 and the connecting rod 330, respectively, are greatly reduced by the roller bearings 329*a* and 329*b* and the ball bearing 331, and in the end, vibrations and noises can not only be reduced, but also a lowering in driving output of the driving motor 17 can be prevented.

Figure 18:
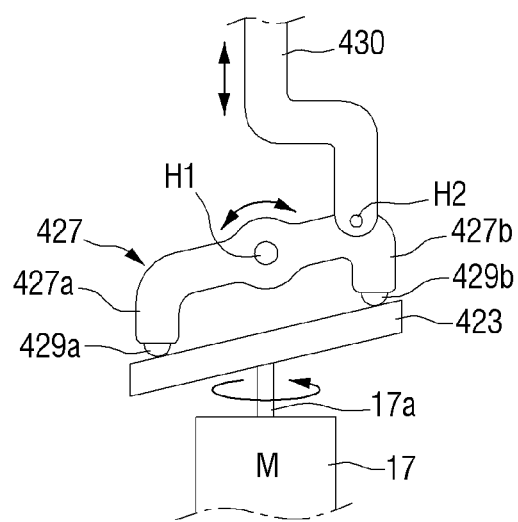

Referring to FIG. 18, another example of cam structure is provided with a cam member 423 in the form of approximately plate, which is inclined to one side and a center of which is coupled with the driving axis 17*a* of the driving motor 17. Further, a cam link 427 is disposed between the connecting rod 430 and the cam member 423.

The cam link 427 at a middle thereof is coupled to the fixing tube 21 (see FIG. 5) by a hinge H1 to coincide with a line of center axis of the driving axis 17*a* and at one side thereof is coupled to the connecting rod 430 by a hinge H2. Further, the cam link 420 has a pair of extended portions 427*a* and 427*b* bent toward the cam member 423 from both sides thereof. The pair of extended portions 427*a* and 427*b* has ball bearings 429a and 429*b* installed on portions where they come in contact with the cam member 423.

In the cam structure as described above, in driving of the driving motor 17, when the cam member 423 is rotated, the connecting rod 430 is traveled back and forth to in turn move the tattoo needle 60 back and forth as the cam link 427 is pivoted left and right on the hinge H1 by the cam member 423.

Even in case of such a cam structure, since the pair of ball bearings 429*a* and 429*b* are disposed on contact portions between the cam link 427 and the cam member 423, vibrations and noises can be reduced and a lowering in driving output can be prevented.

Figure 19:
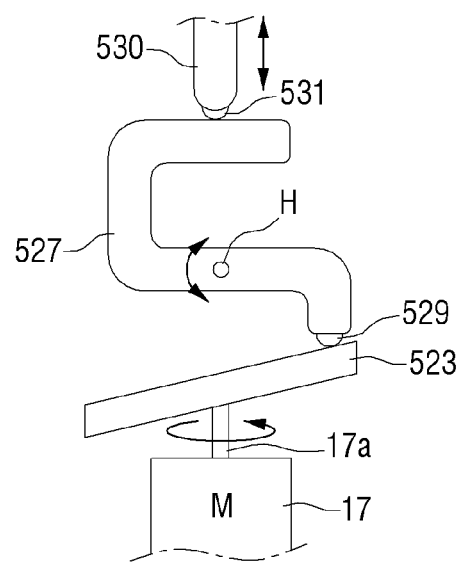

Referring to FIG. 19, further another example of cam structure is provided with a cam member 523 in the form of approximately plate, which is inclined to one side and a center of which is coupled with the driving axis 17*a* of the driving motor 17, like the cam structure shown in FIG. 18.

On the other hand, a cam link 527 at an approximately middle thereof is coupled to the fixing tube 21 (see FIG. 5) by a hinge H and at a lower end thereof is in contact with an upper surface of the cam member 523 through a ball bearing 529. Further, the cam link 527 at a front end thereof is in contact with a connecting rod 530 through another ball bearing 531 installed on a rear end of the connecting rod 530.

As described above, the cam link 527 is disposed in a rolling contact with the cam member 523 and the connecting rod 530 therebetween through the ball bearings 529 and 531. Accordingly, even in case of the cam structure shown in FIG.

19, vibrations and noises can be reduced and a lowering in driving output can be prevented.

Although the bearing structures as described above have been explained as employing the ball bearings, the present invention is not limited thereto and they can also employ the roller bearings.

Although representative embodiment of the present invention has been shown and described in order to exemplify the principle of the present invention, the present invention is not limited to the specific exemplary embodiment. It will be understood that various modifications and changes can be made by one skilled in the art without departing from the spirit and scope of the invention as defined by the appended claims.

The invention claimed is:

1. A tattooing apparatus, comprising:
   a tattoo needle; and
   a cam structure comprising:
      a cam plate that is inclined to one side and is rotatable by a driving motor;
      a connecting rod to transmit a power to the tattoo needle;
      a cam link that moves linearly in connection with rotation of the cam plate to transmit power to the connecting rod; and
      a bearing member disposed at a side of the cam link to come into rolling contact with upper and lower ends of the one side of the cam plate to reduce vibrations and noises.

2. The tattooing apparatus as claimed in claim 1, wherein the cam link comprises:
   a link column;
   an upper link bar projected at one side of the link column and hinged with one end of the connecting rod; and
   a pair of supporting protrusions projected at one side of the link column and disposed in a spaced-apart relation with each other to allow the one side of the cam plate to be inserted therein.

3. The tattooing apparatus as claimed in claim 2, wherein the bearing member comprises a pair of bearing members rotatably coupled to the pair of supporting protrusions, respectively, to come in rolling contact with upper and lower ends of the cam plate.

4. The tattooing apparatus as claimed in claim 1, wherein the cam link is disposed to pass through the cam member and have a rear end slidably inserted coaxial with a driving axis of the driving motor to rotate with the driving axis in connection with a rotation of the driving axis, thus to transmit a power to the connecting rod, which in turn transmits the power to the tattoo needle.

5. The tattooing apparatus as claimed in claim 4, wherein the bearing member is disposed at one side of the cam link to come in rolling contact with the cam member and disposed at a rear end of the connecting rod to come in rolling contact with a front end of the cam link.

6. The tattooing apparatus as claimed in claim 1, wherein the cam link transmits power to the connecting rod, which in turn transmits the power to the tattoo needle while reciprocally pivoting left and right in connection with a rotation of the cam member.

7. The tattooing apparatus as claimed in claim 6, wherein the bearing member is disposed at a portion where the cam link and the cam member are in contact with each other.

8. The tattooing apparatus as claimed in claim 7, wherein the connecting rod has a lower end hinged to a side of the cam link or configured to come in rolling contact with and by the bearing member.

9. The tattooing apparatus as claimed in claim 7, wherein the cam link is in rolling contact with one of both sides of a cam plate through the bearing member.

10. The tattooing apparatus as claimed in claim 1, wherein the bearing member comprises a pair of roller bearings or a pair of ball bearings.

11. The tattooing apparatus as claimed in claim 1, further comprising:
    a first casing having the tattoo needle slidably accommodated therein;
    a second casing having the driving motor; and
    needle adjusting means to connect the first and the second casings and to adjust a degree where the tattoo needle is projected from the first casing by changing a coupling length between the first and the second casings to allow the first casing to approach the second casing or move away from the second casing.

12. The tattooing apparatus as claimed in claim 11, wherein the needle adjusting means comprises a rotation nut to rotate clockwise and counterclockwise.

13. The tattooing apparatus as claimed in claim 12, further comprising:
    an intermediate casing disposed in the first and the second casing to support the connecting rod, and providing a rotation groove in which the rotation nut is rotatably seated.

14. The tattooing apparatus as claimed in claim 13, wherein the needle adjusting means further comprises an inner nut screwed coaxial with the rotation nut on an outer surface of the intermediate casing.

15. The tattooing apparatus as claimed in claim 14, wherein the inner nut has a stopper for maintaining rotation and constant positions of the rotation nut, projected outward at a lower end thereof, and a threaded adjusting portion of a rear end of the first casing is screwed with the rotation nut in a space between the inner nut and the rotation nut.

16. The tattooing apparatus as claimed in claim 1, further comprising:
    a needle cartridge having a needle slider to support the tattoo needle,
    wherein the connecting rod has a joint hooked and coupled with the needle slider to be capable of being separated therefrom and assembled therewith.

17. The tattooing apparatus as claimed in claim 16, wherein the joint comprises:
    an elongated rectangular joint hole in which a hanging hook projected from both sides of a lower end of the needle slider coupled is accommodated; and
    a hook hole formed to penetrate a side of the joint thus to allow the hanging hook to be fitted therein when the hanging hook rotates at an angle of 90 degrees along with the needle slider.

18. The tattooing apparatus as claimed in claim 17, wherein the connecting rod is formed of a hollowed tube, and a linear reciprocating movement of the connecting rod is guided by an anti-vibration tube wrapping the connecting rod.

19. The tattooing apparatus as claimed in claim 18, wherein the anti-vibration tube has an anti-vibration packing fitted between an inner side of the tattooing apparatus and an outer side of the anti-vibration tube to prevent vibrations and slips thereof.

20. A tattooing apparatus, comprising:
    a tattoo needle;
    a cam structure comprising:
        a cam member having a cam plate driven to be rotated by the driving motor and disposed to incline to one side; and a cam link to transmit power to a connecting rod, which in turn transmits the power to the tattoo needle, by reciprocally pivoting back and forth in connection with a rotation of the cam member;

a first casing having the tattoo needle slidably accommodated therein;

a second casing having the driving motor; and needle adjusting means to connect the first and the second casings and to adjust a degree where the tattoo needle is projected from the first casing by changing a coupling length between the first and the second casings to allow the first casing to approach the second casing or move away from the second casing.

21. The tattooing apparatus as claimed in claim 20, wherein the needle adjusting means comprises a rotation nut to rotate clockwise and counterclockwise.

22. The tattooing apparatus as claimed in claim 21, further comprising:

an intermediate casing disposed in the first and the second casing to support the connecting rod, and providing a rotation groove in which the rotation nut is rotatably seated.

23. The tattooing apparatus as claimed in claim 22, wherein the needle adjusting means further comprises an inner nut screwed coaxial with the rotation nut on an outer surface of the intermediate casing.

24. The tattooing apparatus as claimed in claim 23, wherein the inner nut has a stopper for maintaining rotation and constant positions of the rotation nut, projected outward at a lower end thereof, and a threaded adjusting portion of a rear end of the first casing is screwed with the rotation nut in a space between the inner nut and the rotation nut.

25. The tattooing apparatus as claimed in claim 20, further comprising:

a needle cartridge having a needle slider to support the tattoo needle, wherein the connecting rod has a joint hooked and coupled with the needle slider to be capable of being separated therefrom and assembled therewith.

26. The tattooing apparatus as claimed in claim 25, wherein the joint comprises:

an elongated rectangular joint hole in which a hanging hook projected from both sides of a lower end of the needle slider coupled is accommodated; and a hook hole formed to penetrate a side of the joint thus to allow the hanging hook to be fitted therein when the hanging hook rotates at an angle of 90 degrees along with the needle slider.

27. The tattooing apparatus as claimed in claim 25, wherein the connecting rod is formed of a hollowed tube, and a linear reciprocating movement of the connecting rod is guided by an anti-vibration tube wrapping the connecting rod.

28. The tattooing apparatus as claimed in claim 27, wherein the anti-vibration tube has an anti-vibration packing fitted between an inner side of the tattooing apparatus and an outer side of the anti-vibration tube to prevent vibrations and slips thereof.

* * * * *